United States Patent [19]

Reinhoudt et al.

[11] 4,152,335
[45] * May 1, 1979

[54] MACROCYCLIC POLYETHERS

[75] Inventors: David N. Reinhoudt; Robin Th. Gray, both of Amsterdam, Netherlands

[73] Assignee: Shell Oil Company, Houston, Tex.

[ * ] Notice: The portion of the term of this patent subsequent to Feb. 7, 1995, has been disclaimed.

[21] Appl. No.: 857,541

[22] Filed: Dec. 5, 1977

Related U.S. Application Data

[62] Division of Ser. No. 664,331, Mar. 5, 1976, Pat. No. 4,072,693.

[30] Foreign Application Priority Data

Mar. 14, 1975 [GB] United Kingdom ............... 10744/75

[51] Int. Cl.$^2$ ........................................... C07D 317/00
[52] U.S. Cl. .................................................. 260/338
[58] Field of Search ........................ 260/338, 332.3 H; 252/186

[56] References Cited

U.S. PATENT DOCUMENTS 4,072,693  2/1978  Reinhoudt et al. .................. 260/338

Primary Examiner—Alan Siegel

[57] ABSTRACT

Macrocyclic polyethers, their preparation, complexes of these macrocyclic polyethers and their preparation are described.

5 Claims, No Drawings

MACROCYCLIC POLYETHERS

This is a division of application Ser. No. 664,331, filed Mar. 5, 1976, now U.S. Pat. No. 4,072,693, issued Feb. 7, 1978.

BACKGROUND OF THE INVENTION

Many macrocyclic polyethers known from British Patent Number 1,285,367 are hygroscopic. This constitutes a disadvantage because water-containing macrocyclic polyethers are usually unsuitable for application in non-aqueous media. Therefore, special precautions have to be taken to avoid contact of these known polyethers with moist air or water. The macrocyclic polyethers known from British Patent Number 1,108,921 are not hygroscopic, but their preparation requires a rather high temperature, usually between 90° C. and 140° C., and a long reaction time usually between 6 and 24 hours.

This invention provides macrocyclic polyethers which are not hygroscopic and may be prepared at lower temperatures with the application of shorter reaction times.

SUMMARY OF THE INVENTION

The invention may be defined as relating to macrocyclic polyethers of the general formulas

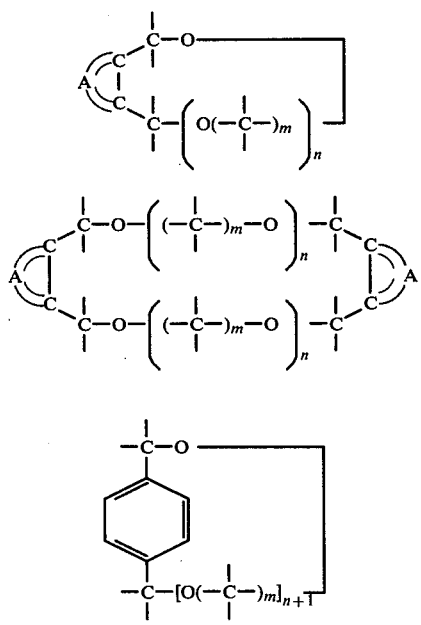

in which formulas A and the two carbon atoms attached to A together represent a carbocyclic aromatic or hetero-aromatic group, m, and n integers from 2 to 10 inclusive and of at least 2, respectively.

These macrocyclic polyethers are prepared by the reaction of vicinal di-(C-Z)-substituted carbocyclic aromatic compounds with functionally terminated (Y) linear polyethers where Z is a halogen and Y is an OM where M is an alkali-metal atom and where Z is OM and Y is a p-tosylate. The crown ethers (macrocyclic polyethers) form complexes with cations of a size that fit into the middle of the crown.

DESCRIPTION OF THE PREFERRED EMBODIMENTS

The macrocyclic polyethers have the general formulas

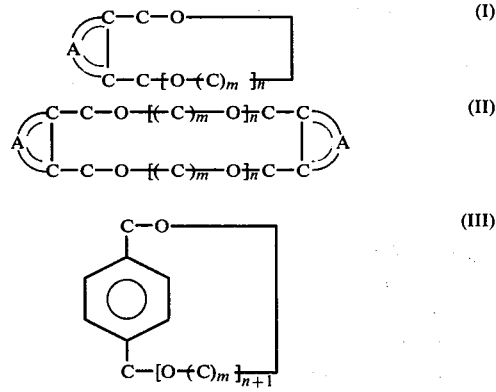

A and the two carbon atoms attached to A together represent a carbocyclic aromatic group, for example, a 1,2-or 2,3-naphthylene group or a 1,2-or 2,4-anthrylene group, or, as is preferred, an o-phenylene group. A and the two carbon atoms attached to A can represent hetero aromatic compounds which are defined as in Kirk-Othmer, "Encyclopedia of Chemical Technology", Second Edition, Volume 2 (1963), page 702: obtained by replacement of one or more carbon atoms of a carbocyclic aromatic compound by a heteroatom, for example, pyridine, pyrimidine, pyrazine, quinoline and isoquinoline and also include those heterocyclic compounds having five-membered rings which show aromatic characteristics and are mentioned on page 703 of said volume, for example, thiophene, pyrrole, furan, indole and benzothiophene. Among the heteroaromatic groups the 2,3-furylene and 2,3-thienylene and particularly the 3,4-furylene and 3,4-thienylene groups are preferred.

The value of m ranges from 2 to 10 inclusive, preferably 2 to 6 inclusive. The order of preference generally decreases as m increases from two, m preferably being equal to two. The values of n is preferably from 2 to 15 inclusive.

A molecular model of a macrocyclic polyether according to the invention looks like a crown, hence they are called "crown" compounds.

The group A in the formulas I and II and the p-phenylene group in the formula III may be unsubstituted or substituted with, for example, alkyl, cycloalkyl, aryl or alkoxy groups or halogen atoms, and may fused with a non-aromatic ring, for example, a 1,3-dioxolane ring. The macro polyethers can be chloromethylated, nitrated, halogenated or sulphonated on the carbocyclic aromatic or hetero aromatic groups(s). Each of the carbon atoms exclusively forming part of the polyether ring may carry one or more substituents, for example, hydrocarbyl or hydrocarbyloxy groups, such as alkyl groups, but preferably carries two hydrogen atoms.

A process for the preparation of the macrocyclic polyethers of the general formulas I and II comprises reacting a vicinal

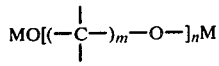
di-(—CX)-substituted carbocyclic aromatic or hetero-aromatic compound, in which X represents a halogen atom, with a compound of the general formula

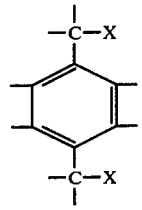
(IV)

wherein M represents an alkali-metal atom, and m and n have the same meanings as in formulas I and II.

A process for the preparation of the macrocyclic polyethers of the general formula III comprises reacting a compound of the general formual

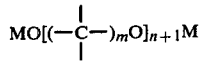
(V)

wherein X represents a halogen atom, with a compound of the general formula

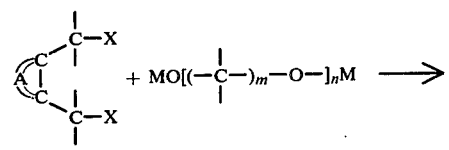
(VI)

wherein M represents an alakli-metal atom and m and n have the same meanings as in formula III.

The formation of macrocyclic polyethers according to formula I may be illustrated by the general equation:

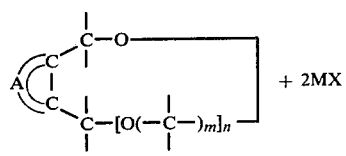
(1)

in which A, M, X, m and n have the above-mentioned meanings.

The formation of macrocyclic polyethers according to formula II may be illustrated by means of the general equation:

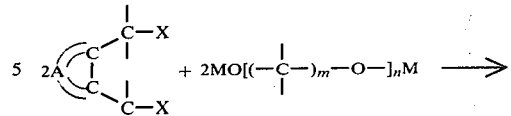
(2)

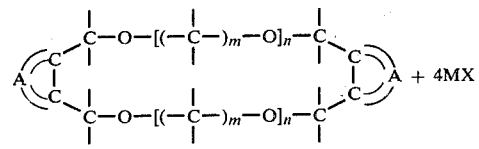

in which A, M, X, m and n have the above-mentioned meanings.

The formation of macrocyclic polyethers according to formula III may be illustrated by means of the general equation:

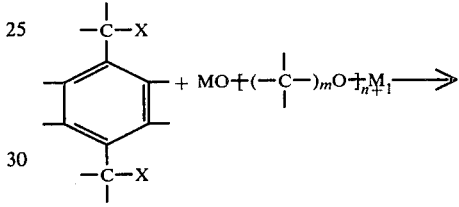
(3)

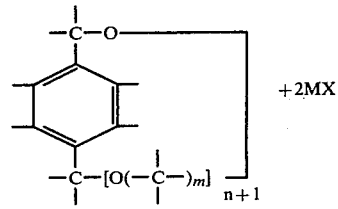

in which M, X, m and n have the above-mentioned meanings.

Another process for the preparation of the macrocyclic polyethers of the general formulas I and II comprises reacting a vicinal

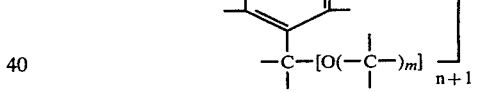
di-(—C—O—M)— substituted carbocyclic aromatic or hetero-aromatic compound, in which M represents an alkali-metal atom, with a compound of the general formula

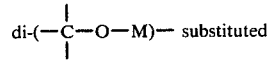
(VII)

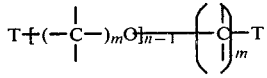

in which T represents a p-tosylate group and m and n have the same meanings as in formulas I and II.

Equation (4) illustrates this process for the preparation of compounds of the general formula I:

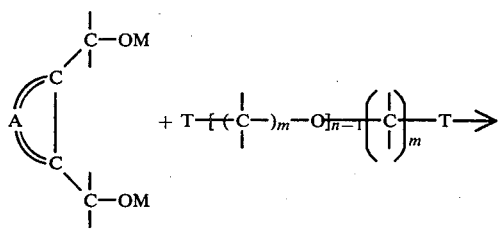

(4)

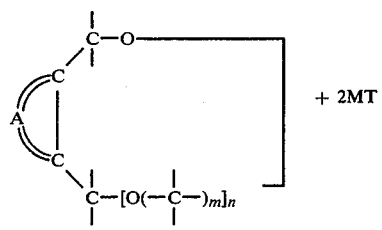

in which A, M, T, m and n have the above-mentioned meanings.

Equation (5) illustrates this process for the preparation of compounds of the general formula II:

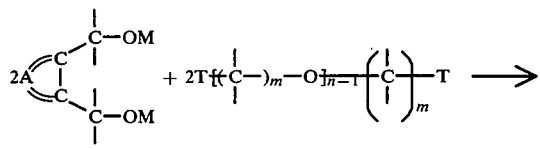

(5)

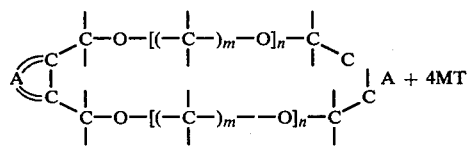

in which A, M, T, m and n have the above-mentioned meanings.

Similarly, macrocyclic polyethers of the general formula III may be prepared by reacting a compound of the general formula VIII (VIII)

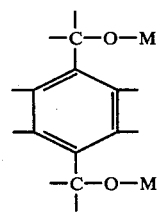

wherein M represents an alkali metal atom, with a compound of the general formula (IX)

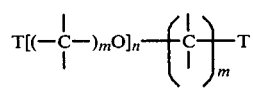

wherein T represents a p-tosylate group and m and p have the same meanings as in the general formula III. This is illustrated by equation (6).

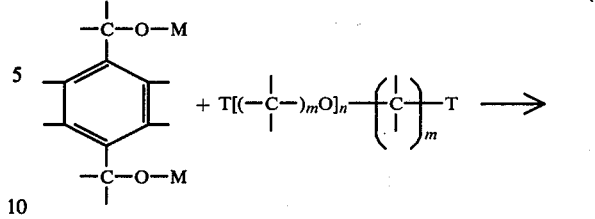

(6)

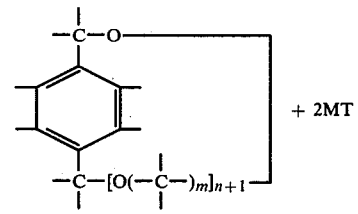

(A particularly useful way of viewing the formulas presented above is illustrated below:

The aromatic starting materials can be viewed as (a) 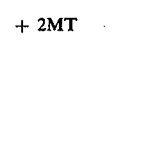 and (b) 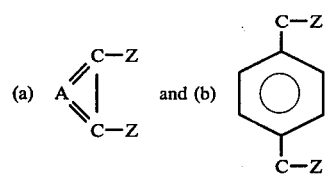

where Z is a halogen or OM where M is as defined above, an alkali-metal atom.

The linear polyether starting materials can be viewed as

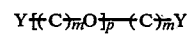

where Y is a OM when Z is a halogen and Y is a p-tosylate when Z is OM and p is n-1 when the aromatic starting material is (a) and n when the aromatic starting material is (b), m and n are defined as above.)

The starting materials for the said processes for the preparation of the macrocyclic polyethers according to the invention will generally be used in equimolar quantities. The specific reactants will determine the details of the preparation with respect to the yield of the macrocyclic polyether being prepared. Usually, both macrocyclic polyethers of the formulas I and II will be formed.

The compounds of the general formulas IV and VI and the vicinal

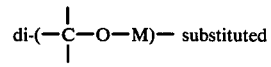

aromatic compounds may be prepared in advance, in the absence of the other reactants, but preferably they are generated in situ from the corresponding diol

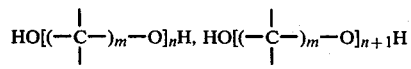

or vicinal

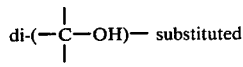

carbocyclic aromatic or heteroaromatic compound, respectively, and the corresponding metal M or a base containing an ion of metal M. Very good results have been obtained with hydrides and alcoholates of metal M. Other examples of suitable bases are alkali-metal hydroxides, such as sodium hydroxide and potassium hydroxide, alkyl derivatives of alkali metals such as n-butyllithium, and quaternary ammonium and phosphonium hydroxides, such as tetramethyl- and tetraethylammonium hydroxide.

The temperature at and the reaction time during which the reactions represented by the equations (1), (2), (3), (4), (5) and (6) are conducted are not critical and may be varied within a wide range. The most suitable temperature and reaction time for a particular case can easily be determined by means of simple experiments. Very good results are usually obtained when the reactions represented by the equations (1), (2) and (3) are conducted at a temperature of from 25° C. to 70° C. when X represents a bromine atom and of from 60° C. to 110° C. when X represents a chlorine atom. If desired, temperatures below 25° C. and above 110° C. may be used, in the range of, for example, 10° C. to 130° C. The preferred reaction time for the reactions represented by the equations (1), (2) and (3) is between 0.5 and 6 hours when as base a hydride or an alcoholate of metal M is used. If desired, reaction times outside this range may be used, but these usually do not give better results. Reaction times between 1 and 5 days are usually required when the reactions represented by the equations (1), (2) and (3) are conducted with an alkyl derivative of an alkali metal as a base and between 10 and 24 hours when the macrocyclic polyethers are prepared according to equations (4), (5) and (6), irrespective of the base applied.

The macrocyclic polyethers according to the invention may be prepared in the absence or — as is preferred — in the presence of a solvent. Examples of solvents are aromatic solvents (benzene, toluene, o-, m-and p-xylene, nitrobenzene, chlorobenzene), dimethylformamide, dimethyl sulphoxide, tetramethylene sulphone — also named sulfolane — and ethers (tetrahydrofuran, dioxan, dialkyl ethers of ethylene glycol).

When the concentrations of the reactants are both decreased to the same extent, the total yield of macrocyclic polyethers remains about the same, but a decrease is observed in the yield of the macrocyclic polyethers of formula (I) and (III). In view of this the reactants are preferably used in starting concentrations of at least 0.1 molar, when macrocyclic polyethers of formula (I) and (III) are desired.

When sodium is used as the metal M, the percentage of the macrocyclic polyethers obtained according to equation (1) constitutes of the sum of these compounds and the macrocyclic polyethers obtained according to equation (2) is highest when m and n are equal to 2 and 4 respectively. When potassium is used as the metal M, this percentage is highest when m and n are equal to 2 and 6, respectively. Considerably higher maximum percentages are obtained with potassium than with sodium.

The macrocyclic polyethers can be isolated from the reaction mixture by conventional techniques. For example, the reaction mixture is cooled in ice, a precipitate of an alkali-metal halide is filtered off and the filtrate obtained is boiled down, after which the residue is subjected to distillation at sub-atmospheric pressure to isolate the macrocyclic polyethers formed.

The macrocyclic polyethers are capable of forming complexes with a salt having a compatible cation as hereinafter defined. The cation is present in the polyether ring. Each polyether ring contains one cation, so that the valency of a ring containing a cation is that of the cation itself. Consequently, one anion of a salt forming such a complex is electrically equivalent to the same number of cations of the complex as of the salt itself. Organic or inorganic cations may be present in polyether rings, for example, those derived from primary amines by taking up a proton, but preferably those of metals of Group I, II or III of the Periodic Table of the Elements.

The propensity to form these complexes depends on the ratio between the diameter of the cation and the dimensions of the cavity within the polyether ring and on the positions of the oxygen atoms in the polyether ring. The most stable complexes are those in which the diameter of the cation is somewhat smaller than the internal dimensions of the polyether ring and in which the location of the oxygen atoms is as symmetrical as possible. For example, the macrocyclic polyethers obtained in reaction (1) in which m=2 and n=4 can very easily accommodate a sodium ion and those in which m=2 and n=6, a potassium ion. The macrocyclic polyethers obtained by reaction (3) in which m=2 and n=3 can easily accommodate a potassium ion. Thus, the words "compatible cation" used therein refer to a cation which can be accommodated in the polyether ring of the macrocyclic polyether, because the size of the cation and the internal dimensions of the ring are mutually compatible.

Table I presents some examples of these complexes of macrocyclic polyethers of formulas I and II with a salt having a compatible cation. The value for m is equal to 2.

Table I

| n | compatible cations |
|---|---|
| 1 | none |
| 2 | Li+ |
| 3 | Li+, Na+, K+, NH4+, Ca++, mono- and dihydrocarbyl-ammonium ions |
| 4 | Li+, Na+, K+, NH4+, Ca++, mono- and dihydrocarbyl-ammonium ions |
| 5 | Li+, Na+, K+, NH4+, mono- and dihydrocarbyl-ammonium ions, Sr++, Rb+, Cs+ |
| 6 | Li+, Na+, K+, NH4+, Ca++, mono- and dihydrocarbyl-ammonium ions, Sr++, Rb+, Cs+ |
| 7 | Li+, Na+, K+, NH4+, Ca++, mono- and dihydrocarbyl-ammonium ions, Sr++, Rb+, Cs+. |

The invention also relates to a process for the preparation of the above-mentioned complexes by mixing the macrocyclic polyethers according to the invention and a salt having a compatible cation in a solvent. The macrocyclic polyether and the salt are preferably used in amounts corresponding to one molecule of the polyether per cation of the salt. This process may be conducted at sub-ambient, ambient or super-ambient temperatures. Some complexes are not sufficiently stable to permit isolation from the solution. Sufficiently stable complexes may be isolated by cooling, and by filtering, washing and drying the precipitate-formed. Examples of suitable solvents are methanol, ethanol, isopropanol, sec-butanol, acetone, butanone, chloroform, dichloromethane, tetrachloromethane, benzene, toluene, o-, m-and p-xylene.

The macrocyclic polyethers obtained according to the invention may be used as a solubilizing agent for salts in non-aqueous media in which they are normally insoluble. For example, potassium hydroxide solubilized by 3,4-benzo-1,6,9,12,15,18,21-heptaoxacyclotricos-3-ene in an aprotic medium may be employed as a soluble acid acceptor, to initiate anionic polymerization, for example, of acrylonitrile, and to saponify esters. Sodium or potassium permanganate solubilized by this polyether may be used as an oxidizing agent.

The invention is further illustrated by means of the following Illustrative Embodiments. These Embodiments are for the purpose of illustration only and should not be construed so as to limit the scope of the invention. The macrocyclic polyethers formed are of the general formulas I, II or III, in which the carbon atoms of the polyether ring carry hydrogen atoms and m is equal to two. In the Illustrative Embodiments I-XII, XVI and XVII a three-necked, round-bottomed flask fitted with a gas inlet tube, dropping funnel and a $CaCl_2$-protected condenser was used.

ILLUSTRATIVE EMBODIMENT I

A 1-litre flask was charged with 0.04 mol of hexaethylene glycol, 0.084 mol of freshly sublimed potassium tert-butoxide and 300 ml of sodium-dried toluene. This mixture was magnetically stirred under argon at 60° C. for one hour.

After cooling to 22° C. a solution of 0.04 mol of 1,2-bis(bromomethyl)benzene in 100 ml of dry toluene was added. The mixture was then heated under nitrogen at 60° C. for 30 minutes.

The reaction mixture was cooled to 0° C., filtered (No. 3 sintered glass filter) and the precipitated KBr washed with 50 ml of dry toluene. The combined filtrate and washings were boiled down and the resultant brown oil filtered through a column containing 160g of neutral aluminum oxide with 250 ml of tetrahydrofuran, giving 9.8g of an oil containing the macrocyclic polyethers formed. This amounts to a total yield of 63% of macrocyclic polyethers. Distillation at 200° C./0.01 mm Hg gave 7.72 g of 3,4-benzo-1,6,9,12,15,18,21-heptaoxacyclotricos-3-ene as a colourless oil (formula I, A forming an o-phenylene group, n=6), the yield being 50%, calculated on 1,2-bis(bromomethyl)benzene.

ILLUSTRATIVE EMBODIMENT II

A 500-ml flask was charged with 0.02 mol of triethylene glycol and 0.042 mol of freshly sublimed potassium tert-butoxide in 150 ml of dry toluene. The compounds were allowed to react for one hour under nitrogen at 60° C. After cooling to 22° C., a solution of 0.02 mol of 1,2-bis(bromomethyl)benzene in 50 ml of dry toluene was added, and the mixture was heated under argon at 60° C. for one hour.

The reaction mixture was cooled to 0° C., the potassium bromide filtered off, and the precipitate washed with 50 ml of dry toluene. The combined filtrate and washings were boiled down and the resulting oil filtered through aluminum oxide with tetrahydrofuran, giving 3.4 g of an oil, which corresponds to a total yield of macrocyclic polyethers of 78%. Distillation at 160° C./0.01 mm Hg gave 0.41 g of 3,4-benzo-1,6,9,12-tetraoxacyclotetradec-3-ene as a colourless oil (formula I, A forming an o-phenylene group, n=3) and at 250° C. 1,2 g of 3,4,17,18-dibenzo-1,6,9,12,15,20,23,26-octaoxacyclooctacos-3,17-diene (formula II, A forming an o-phenylene group, n=3) as a colourless oil, which solidified on standing; the yields of these compounds were 8% and 24%, respectively, calculated on 1,2-bis(bromomethyl)benzene.

ILLUSTRATIVE EMBODIMENT III

In a 500-ml flask 0.02 mol of triethylene glycol was reacted with 0.044 mol of n-butyllithium — as a 20% w solution in n-hexane — in 150 ml dry toluene for one hour under argon at 22° C. Subsequently, a solution of 0.02 mol of 1,2-bis(bromomethyl)benzene in 50 ml dry toluene was added, and the mixture refluxed under nitrogen for 72 hours.

The reaction mixture was cooled to 0° C. and the cream-coloured solid — a mixture of LiBr and LiBr.macroyclic polyether complex-filtered off. After drying in a vacuum desiccator the solid complex (7.35 g) was suspended in 50 ml of water and the suspension three times extracted with 50 ml of chloroform. The combined extracts were dried over magnesium sulphate and then boiled down, giving 4.0 g of an orange oil. Distillation at 150° C./0.01 mm Hg gave a fraction of 1.26 g of 3,4-benzo-1,6,9,12-tetraoxacyclotetradec-3-ene as a colourless oil (formula I, A forming an o-phenylene group, n=3) the yield being 25%, calculated on 1,2-bis(bromomethyl)benzene.

ILLUSTRATIVE EMBODIMENT IV

Ten experiments starting from various glycols and bases were conducted in a manner comparable to the experiments described in Illustrative Embodiments I and II. The glycols and bases used are stated in Table II, first and second column from the left, respectively. The letter n in the first column has the same meaning as in equations (1) and (2). The third column from the left presents the total yield of macrocyclic polyethers — defined as all the material which can be eluded with tetrahydrofuran through a column of neutral aluminium oxide —, calculated on 1,2-bis(bromomethyl)benzene, and the fourth column the percentage of the compound of formula I in the eluded material calculated on total macrocyclic polyethers. The yields of the macrocyclic polyethers of formulas I and II, calculated on 1,2-bis(bromomethyl)benzene and found after distillation, are presented in the second and first column from the right, respectively. Table II also includes the results of Illustrative Embodiments I, II and III.

Table II

| Glycol | | Total yield of macrocyclic polyethers, | % of compound of formula I in macrocyclic poly- | Yield', % of macrocyclic polyether of formula | |
|---|---|---|---|---|---|
| n | Base | % | ethers | I | II |
| 2 | NaH | 39 | — | 1.1 | 17 |
|   | KO-tert-$C_4H_9$ | 41 | — | — | — |
| 3 | NaH | 50 | 27 | 10 | 14 |

Table II-continued

| Glycol n | Base | Total yield of macrocyclic polyethers, % | % of compound of formula I in macrocyclic polyethers % | Yield', % of macrocyclic polyether of formula | |
|---|---|---|---|---|---|
| | | | | I | II |
| | KO-tert-C$_4$H$_9$ | 78 | 15 | 8 (Illustrative Embod.II) | 24 |
| 4 | NaH | 61 | 79 | 34 | — |
| | KO-tert-C$_4$H$_9$ | 69 | 44 | 24 | 8 |
| 5 | NaH | 62 | 55 | 29 | — |
| | KO-tert-C$_4$H$_9$ | 71 | 89 | 53 | — |
| 6 | NaH | 54 | 60 | 18 | — |
| | KO-tert-C$_4$H$_9$ | 63 | 96 | 50 | — |
| 7 | NaH | 45 | 63 | 22 | — |
| | KO-tert-C$_4$H$_9$ | 54 | 87 | 43 | — |
| 3 | Li-n-C$_4$H$_9$ | | | 25 (Illustrative Embod.III) | — |

' After distillation

Table III presents some spectral properties of the macrocyclic polyethers obtained.

Table III

| Compound of formula | n | Mass Spectrum M$^+$ | PMR H$_a$'(ppm) | CMR C$_A$*(ppm) | Name of the compound |
|---|---|---|---|---|---|
| I | 2 | 208 | 4.662 | 69.994 | 3,4-benzo-1,6,9-trioxacyclo-undec-3-ene |
| I | 3 | 252 | 4.786 | 69.344 | 3,4-benzo-1,6,9,12-tetraoxa-cyclotetradec-3-ene |
| I | 4 | 296 | 4.727 | 69.734 | 3,4-benzo-1,6,9,12,15-penta-oxacycloheptadec-3-ene |
| I | 5 | 340 | 4.685 | 69.929 | 3,4-benzo-1,6,9,12,15,18-hexa-oxacycloeicos-3-ene |
| I | 6 | 384 | 4.678 | 69.864 | 3,4-benzo-1,6,9,12,15,18,21-heptaoxacyclotricos-3-ene |
| I | 7 | 428 | 4.672 | 69.734 | 3,4-benzene-1,6,9,12,15,18,21,24-octaxacyclohexacos-3-ene |
| II | 2 | 416 | 4.623 | 69.734 | 3,4,14,15-dibenzo-1,6,9,12,17,20-hexaoxacyclodocos-3-ene |
| II | 3 | 504 | 4.659 | 69.799 | 3,4,17,18-dibenzo-1,6,9,12,15,20,23,26-octaoxacyclooctacos-3,17-diene |
| II | 4 | 592 | 4.639 | 69.734 | 3,4,20,21-dibenzo-1,6,9,12,15,18,23,26,29,32-decaoxacyclo-tetratriacont-3,20-diene |

' refers to the H atoms in the CH$_2$ groups attached to the benzene ring
*refers to the C atoms in the CH$_2$ groups attached to the benzene ring

ILLUSTRATIVE EMBODIMENT V

In a 1-litre flask 0.04 mol of tetraethylene glycol was reacted with 0.09 mol of sodium hydride in 300 ml of dry toluene for one hour under nitrogen at 60° C. Subsequently 0.04 mol of 1,2-bis(chloromethyl)benzene dissolved in 100 ml toluene was added and the mixture obtained was stirred for four hours at 100° C.

The reaction mixture was cooled to 0° C. and the sodium chloride (4.70 g) filtered off. The filtrate was boiled down to give 10.7 g of an oil. Distillation at 160° C./0.01 mm Hg gave a fraction of 4.03 g of 3,4-benzo-1,6,9,12,15-pentaoxacycloheptadec-3-ene as a colourless oil (formula I, A forming an o-phenylene group, n=4). The yield was 34%, calculated on 1,2-bis(chloromethyl)benzene.

ILLUSTRATIVE EMBODIMENT VI

In a 250-ml flask 0.01 mol 1,2-bis(hydroxymethyl)-benzene was reacted with 0.021 mol of sodium hydride in 75 ml of dry toluene for one hour under nitrogen at 50° C. Subsequently a solution of 0.01 mol of triethylene glycol ditosylate in 25 ml of dry toluene was added, and the reaction mixture refluxed under nitrogen for 16 hours.

After cooling to 22° C., the sodium p-toluenesulphonate was filtered, the precipitate washed with 25 ml of toluene and the combined filtrate and washings boiled down. The resulting oil was filtered through neutral aluminum oxide with tetrahydrofuran to give 2.4 g of a colourless oil, corresponding to a total yield of macrocyclic polyethers of 95%. Distillation of this oil at 160° C./0.01 mm Hg gave 0.18 g of 3,4-benzo-1,6,9,12-tetraoxacyclotetradec-3-ene (formula I, A forming an o-phenylene group, n=3) as a colourless oil and at 250° C. 0.45 g of 3,4,17,18-dibenzo-1,6,9,12,15,20,23,26-octaoxacyclooctacos-3,17-diene (formula II, A forming an o-phenylene group, n=3) as white crystals, the yields of these compounds being 7% and 19%, respectively, calculated on 1,2-bis(hydroxymethyl)benzene.

ILLUSTRATIVE EMBODIMENT VII

Illustrative Embodiment I was repeated three times, each time with a different rate of addition of the toluene solution of 1,2-bis(bromomethyl)benzene, Table IV presents the results.

Table IV

| Addition rate, ml/h | Total yield of macrocyclic polyethers, % | % of compound of formula I in macrocyclic polyethers' |
|---|---|---|
| See Illust. Embod. I | 63 | 94 |
| 22.5 | 66 | 95 |

Table IV-continued

| Addition rate, ml/h | Total yield of macrocyclic polyethers, % | % of compound of formula I in macrocyclic polyethers' |
| --- | --- | --- |
| 12 | 63 | 95 |
| 6 | 35 | 95 |

'After distillation

ILLUSTRATIVE EMBODIMENT VIII

Illustrative Embodiment I was repeated five times with tetraethylene glycol instead of hexaethylene glycol; the concentrations of the 1,2-bis(bromomethyl)benzene in toluene are stated in the left-hand column of Table V. Equimolar quantities of 1,2-bis(bromomethyl)benzene and tetraethylene glycol were used. This table also presents the results.

Table V

| Concentration mol/liter | Total yield of macropolyethers, % | % of compound of formula I in macrocyclic polyethers' |
| --- | --- | --- |
| 0.2 | 49 | 52 |
| 0.1 | 51 | 40 |
| 0.05 | 61 | 44 |
| 0.025 | 68 | 38 |
| 0.01 | 46 | 21 |

'After distillation

ILLUSTRATIVE EMBODIMENT IX

In a 1-litre flask a mixture of 0.04 mol of heptaethylene glycol and 0.084 mol of freshly sublimed potassium-tert-butoxide in 300 ml of dry toluene was stirred under nitrogen for one hour at 50° C. Subsequently a solution of 0.04 mol of 3,4-bis(chloromethyl)furan in 100 ml of toluene was added. The reaction mixture was stirred at 100° C. for four hours and then cooled to 0° C. The precipitated potassium chloride (6.0 g) was filtered off and the filtrate was boiled down at sub-atmospheric pressure to give 7.42 g of an oil. This oil was dissolved in dry tetrahydrofuran and filtered through a column containing 160 g of aluminum oxide. The first fraction, 500 ml, was boiled down at sub-atmospheric pressure to give 4.36 g of a light yellow oil, corresponding to a total yield of macrocyclic polyethers of 52%. Distillation at a pressure of 0.01 mm Hg afforded a fraction of 3.56 g of [3,4-c]furo-1,6,9,12,15,18,21,24-octaoxacyclohexacos-3-ene (formula I, A forming a 3,4-furylene group, n=7), the yield being 43%, calculated on 3,4-bis(chloromethyl)furan.

ILLUSTRATIVE EMBODIMENT X

Several experiments starting from various glycols and bases were conducted in a manner comparable to the experiment described to illustrative Embodiment IX. The glycols and bases are stated in table VI, first and second column from the left, respectively. The letter n in the first column has the same meaning as in equations (1) and (2). The third column from the left presents the total yield of macrocyclic polyethers (defined as in Illustrative Embodiment IV), calculated on 3,4-bis(chloromethyl)furan, and the fourth column the percentage of the compound of formula I,A forming a 3,4-furylene group, calculated on total macrocyclic polyethers. The yields of the compounds according to formulas I and II, calculated on 3,4-bis(chloromethyl)furan and found after distillation, are presented in the second and first columns from the right, respectively. Table VI also includes the result of Illustrative Embodiment IX.

Table VI

| Glycol n | Base | Total yield of macrocyclic polyethers, % | % of compound of formula I in macrocyclic polyethers | Yield*, % of macrocyclic polyether of formula | |
| --- | --- | --- | --- | --- | --- |
| | | | | I | II |
| 2 | KO-tert-$C_4H_9$ | 40 | 0 | 0 | 5 |
| 3 | NaH | 57 | 26 | 8 | 18 |
| | KO-tert-$C_4H_9$ | 55 | 18 | 7 | 18 |
| 4 | NaH | 54 | 80 | 31 | 1 |
| | KO-tert-$C_4H_9$ | 56 | 61 | 19 | 8 |
| 5 | NaH | 36 | 60 | 13 | — |
| | KO-tert-$C_4H_9$ | 48 | 88 | 30 | — |
| 6 | NaH | 73 | 61 | 28 | — |
| | KO-tert-$C_4H_9$ | 64 | 95 | 44 | — |
| 7 | NaH | 53 | 59 | 30 | — |
| | KO-tert-$C_4H_9$ | 52 | 88 | 43' | — |

'Illustrative Embodiment IX
*After distillation

Table VII presents some spectral properties of the macrocyclic polyethers obtained.

Table VII

| Compound of formula | n | Mass Spectrum $M^+$ | PMR $H_a'$ | CMR $C_a^*$(ppm) | Name of the compound |
| --- | --- | --- | --- | --- | --- |
| I | 3 | 242 | 4.577 | 63.560 | [3,4-c]furo-1,6,9,12-tetraoxacyclotetradecane |
| I | 4 | 286 | 4.518 | 63.950 | [3,4-c]furo-1,6,9,12,15-pentaoxacycloheptadecane |
| I | 5 | 330 | 4.499 | 63.560 | [3,4-c]furo-1,6,9,12,15,18-hexaoxacycloeicosane |
| I | 6 | 374 | 4.502 | 63.560 | [3,4-c]furo-1,6,9,12,15,18,21-heptaoxacyclotricosane |
| I | 7 | 418 | 4.486 | 63.560 | furo-1,6,9,12,15,21,24-octaoxacyclotricosane |
| II | 2 | 396 | 4.512 | 63.690 | 3,4,14,15-difuro-1,6,9,12,17,20-hexaoxacyclodocosane |
| II | 3 | 484 | 4.483 | 63.625 | 3,4,17,18-difuro-1,6,9,12,15,20,23, |

Table VII-continued

| Compound of formula | n | Mass Spectrum M+ | PMR H_a' | CMR C_a*(ppm) | Name of the compound |
|---|---|---|---|---|---|
| II | 4 | 572 | 4.476 | 63.560 | 26-octaoxacyclooctacosane 3,4,20,21-difuro-1,6,9,12,15,18,23, 26,29,32-decaoxacyclotetratriacontane |

' refers to the H atoms in the CH₂ groups attached to the furan ring
*refers to the C atoms in the CH₂ groups attached to the furan ring

ILLUSTRATIVE EMBODIMENT XI

In a 1-litre flask 0.04 mol of triethylene glycol was reacted with 0.09 mol of sodium hydride in 300 ml of dry toluene for two hours at 70° C. Subsequently 0.04 mol of 3,4-bis(chloromethyl)furan in 100 ml of toluene was added and the mixture stirred under nitrogen for four hours at 100° C. The precipitated sodium chloride (4.70 g) was filtered off and the filtrate was boiled down at sub-atmospheric pressure to give 9.48 g of an oil. This oil was dissolved in tetrahydrofuran and filtered over aluminium oxide. The first fraction, 500 ml, was boiled down to give 5.52 g of an oil, which was separated by distillation at sub-atmospheric pressure into two fractions:

Fraction I, boiling point 100° C. at 0.01 mm Hg, 0.39 g of [3,4-c]furo-1,6,9,12-tetraoxacyclotetradec-3-ene (formula I, A forming a 3,4-furylene group, n=3), the yield being 8%, calculated on 3,4-bis(chloromethyl)furan, Fraction II, boiling point 220° C. at 0.01 mm Hg, 0.98 g of [3,4-c][17,18-c]difuro-1,6,9,12,15,20,23,26-octaoxacyclooctacos-3,17-diene (formula II, A forming a 3,4-furylene group, n=3), the yield being 18%, calculated on 3,4-bis(chloromethyl)furan.

ILLUSTRATIVE EMBODIMENT XII

In a 1-litre flask 0.05 mol of pentaethylene glycol was reacted with 0.11 mol of potassium tert-butoxide in 350 ml of dry toluene for one hour at 50° C. Subsequently a solution of 0.05 mol of 3,4-bis(chloromethyl)-2,5-dimethylthiophene in 150 ml of toluene was added and the reaction mixture stirred for four hours at 100° C. The potassium chloride which precipitated during the reaction (6.0 g) was filtered off and the filtrate boiled down at sub-atmospheric pressure to give 18.0 g of an oil. This oil was dissolved in tetrahydrofuran and filtered over aluminium oxide. From the first 500 ml of the filtrate 9.92 g of a light yellow oil was isolated, which was distilled at 0.01 mm Hg. At this pressure 8.93 g of [3,4-c]-2',5'-dimethylthieno-1,6,9,12,15,18-hexaoxacycloeicos-3-ene (formula I, A forming a 3,4-thienylene group, n=5) was isolated as a colourless oil, the yield being 48%, calculated on 3,4-bis(chloromethyl)-2,5-dimethylthiophene.

ILLUSTRATIVE EMBODIMENT XIII 0.01 Mol of sodium permanganate was stirred with 100 ml of chloroform at a temperature of 22° C. The permanganate was filtered off; the filtrate was colourless and did not contain any sodium permanganate. The same result was obtained with potassium permanganate. This result was also obtained when the chloroform was replaced by benzene.

0.01 Mol of sodium permanganate was suspended in 100 ml of chloroform and 0.01 mol of 3,4-benzo-1,6,9,12-tetraoxacyclotetradec-3-ene (formula I, A forming an o-phenylene group, n=3) was added to the suspension at a temperature of 22° C. with stirring. The chloroform immediately became purple. This experiment was repeated with the four macrocyclic polyethers stated in Table VIII. The letter "n" refers to formula I, A forming an o-phenylene group. Then, the four macrocyclic polyethers were tested with potassium permanganate in the same manner. Table VIII presents the results. The same results were obtained when benzene was used instead of chloroform.

Table VIII

| Macrocyclic polyether, n | Colour of organic liquid with | |
|---|---|---|
| | NaMnO₄ | KMnO₄ |
| 4 | purple | colourless |
| 5 | purple | colourless |
| 6 | purple | purple |
| 7 | purple | purple |

ILLUSTRATIVE EMBODIMENT XIV

An amount of 0.05 mmol of Zeise's salt —KPtCl₃.CH₂=CH₂— was suspended in 1 ml of chloroform (this salt is insoluble in chloroform). Then 0.05 mmol of 3,4-benzo-1,6,9,12-tetraoxacyclotetradec-3-ene (formula I, A forming an o-phenylene group, n=3) was added at a temperature of 22° C. to the suspension with stirring. This imparted a yellow colour to the chloroform. The solution was analysed by PMR spectroscopy to determine the percentage of Zeise's salt complexed according to the equation:

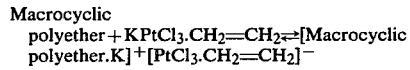

This experiment was repeated with five other macrocyclic polyethers, all belonging to the group of formula I, A forming an o-phenylene group using the values for n stated in Table IX, left-hand column. The six experiments were repeated with the furan derivatives, belonging to the group of formula I, A forming a furan ring, also using the values for n stated in Table IX, left-hand column. Table IX presents the percentage of Zeise's salt complexed, determined by PMR spectroscopy.

Table IX

| n | % complexed with polyether, A forming | |
|---|---|---|
| | an o-phenylene group | a 3,4-furylene group |
| 3 | 11 27 | 60 |
| 4 | 74 | 100 |
| 5 | 98 | 100 |
| 6 | 100 | 100 |
| 7 | 100 | 100 |
| 8 | 100 | not determined |

ILLUSTRATIVE EMBODIMENT XV

A flask was charged with 0,4 mmol of 3,4-benzo-1,6,9,12,15,18-hexaoxacycloeicos-3-ene, 1 ml of deutero chloroform, 0,4 mmol of NH₄PF₆ dissolved in 1 ml of water and 0.4 mmol of tert-butylammonium chloride dissolved in 1 ml of water. The mixture thus obtained was stirred for five minutes and then allowed to separate in two phases. The chloroform layer was dried over anhydrous sodium sulphate. Analysis of the dried chloroform layer by PMR spectroscopy showed that 28% of the tert-butylammonium groups was complexed by the macrocyclic polyether. The complex formed was a hexafluorophosphate. The tert-butylammonium chloride itself is insoluble in chloroform.

ILLUSTRATIVE EMBODIMENT XVI

A 250-ml flask was charged with 0.01 mol of hexaethylene glycol, 0.021 mol of freshly sublimed potassium tert-butoxide and 75 ml of sodium-dried toluene. This mixture was magnetically stirred under nitrogen at 60° C. for two hours.

After cooling down to 22° C. a solution of 0.01 mol of 1,2-bis(chloromethyl)-4,5-methylenedioxybenzene in 25 ml dry toluene was added and the mixture heated under nitrogen at 100° C. for four hours. Subsequently, the mixture was cooled to 0° C., the potassium chloride filtered off and the filtrate evaporated at sub-atmospheric pressure to give 3.91 g of an oil. This oil was dissolved in tetrahydrofuran and filtered over aluminium oxide. From the first 250 ml of the filtrate 1.7 g of a yellow oil was isolated by evaporation, which oil was distilled at 0.01 mm Hg. At this pressure 1.07 g of 3,4-(4′,5′-methylenedioxybenzo)-1,6,9,12,15,18,21-heptaoxacyclotricos-3-ene was isolated as a yellow oil (formula I, A forming a 4,5-methylenedioxy-o-phenylene group, n=6), the yield being 25%, calculated on 1,2-bis(chloromethyl)-4,5-methylene dioxybenzene.

ILLUSTRATIVE EMBODIMENT XVII

A mixture of 0.01 mol of tetraethylene glycol and 0.022 mol of freshly sublimed potassium ter-butoxide in 75 ml of dry toluene was heated under nitrogen at 70° C. for one hour. The mixture was cooled to room temperature and a solution of 0.01 mol of 1,4-bis(bromomethyl)benzene in 25 ml of dry toluene was added. The mixture was then heated under nitrogen at 110° C. for two hours, after which it was cooled to 0° C. and filtered to remove precipitated potassium bromide. The potassium bromide was washed with 10 ml of toluene and the combined filtrate and washings were boiled down. The resulting yellow oil (2.82g, 95% crude yield) was filtered through a column containing 40g of neutral aluminium oxide with 200 ml of tetrahydrofuran, giving 1.3g of an oily solid containing the macrocyclic polyethers formed. This amounts to a total yield of 44% of macrocyclic polyethers. Distillation at 180° C./0.01 mm Hg gave 1.02 g of 3,6-benzo-1,8,11,14-tetraoxacyclohexadec-3,5-diene as a colourless oil (formula III, m=2, p=4), the yield being 35%, calculated on 1,4-bis(bromomethyl)benzene. This oil immediately solidified to a while crystalline solid melting between 55° and 56° C.

Ten experiments starting from various glycols and bases were conducted in a manner comparable to the experiment described in this example. The glycols and bases used are stated in Table X, first and second column from the left, respectively. The letter p in the first column has the same meaning as in equation (3). The third column from the left presents the yield of crude product obtained after boiling down the combined filtrate and toluene washings. The fourth column from the left presents the total yield of macrocyclic polyethers-defined as all the material which can be eluded with tetrahydrofuran through a column of neutral aluminium oxide-, calculated on 1,4-bis(bromomethyl)benzene. The yields of the macrocyclic polyethers of formula III, calculated on 1,4-bis(bromomethyl)benzene and found after distillation, are presented in the first column from the right. No macrocyclic polyethers containing two p-phenylene groups per molecule were obtained upon distillation under reduced pressure.

TABLE X

| Glycol p | Base | Crude product, % | Total yield of macrocyclic polyethers, % | Yield, %, after distillation, of macrocyclic polyether of formula III. |
|---|---|---|---|---|
| 3 | NaH | 82 | 15 | 4 |
| 4 | NaH | 96 | 23 | 5 |
| 4 | KO-tert-$C_4H_9$ | 95 | 44 | 35 |
| 5 | KO-tert-$C_4H_9$ | 99 | 24 | 16 |
| 6 | KO-tert-$C_4H_9$ | 97 | 29 | 6 |
| 7 | KO-tert-$C_4H_9$ | 96 | 27 | 7 |
| 8 | KO-tert-$C_4H_9$ | 100 | 49 | 13 |

Table XI presents some spectral properties of the macrocyclic polyethers thus obtained.

TABLE XI

| Compound of formula III p | Mass spectrum M+ | $H_a$[1] (ppm) | H bound to[2] aromatic ring (ppm) | Polyether ring[3] | Name of Compound |
|---|---|---|---|---|---|
| 3 | 252 | 4.411 | 7.306 | 2.973(s); 3.17–3.30(m); 3.47–3.60(m) | 3,6-benzo-1,8,11,14-tetraoxa-cyclohexadec-3,5-diene |
| 4 | 296 | 4.567 | 7.404 | 3.36–3.56(m) | 3,6-benzo-1,8,11,14,17-pentaoxa-cyclononadec-3,5-diene |
| 5 | 340 | 4.587 | 7.384 | 3.54–3.68(m) | 3,6-benzo-1,8,11,14,17,20-hexa-oxacyclodocosa-3,5-diene |
| 6 | 384 | 4.587 | 7.414 | 3.53–3.67(m) | 3,6-benzo-1,8,11,14,17,20,23-heptaoxacyclopentacosa-3,5-diene |
| 7 | 428 | 4.580 | 7.342 | 3.57–3.65(m) | 3,6-benzo-1,8,11,14,17,20,23,26-octaoxacyclooctacosa-3,5-diene |
| 8 | 472 | 4.603 | 7.368 | 3.64–3.68(m) | 3,6-benzo-1,8,11,14,17,20,23,26,29-nonaoxacyclohentriaconta-3,5-diene |

[1] refers to the H atoms in the $CH_2$ groups attached to the benzene ring.
[2] refers to H atoms bound to the p-phenylene group
[3] s = singlet, m = multiplet

We claim as our invention:

1. The macrocyclic polyether 3,4-benzo-1,6,9-trioxacycloundec-3-ene.

2. The macrocyclic polyether 3,4-benzo-1,6,9,12,15-pentaoxacycloheptadec-3-ene.

3. The macrocyclic polyether 3,4-benzo-1,6,9,12,15,18-hexaoxacycloeicos-3-ene.

4. The macrocyclic polyether 3,4-benzo-1,6,9,12,15,18,21-heptaoxacyclotricos-3-ene.

5. The macrocyclic polyether 3,4-benzo-1,6,9,12,15,18,21,24-octacyclohexacos-3-ene.

* * * * *